United States Patent
Firestone et al.

(12)

(10) Patent No.: US 6,248,354 B1
(45) Date of Patent: Jun. 19, 2001

(54) CAPSULE SYSTEM

(75) Inventors: Bruce A. Firestone, Irvine; Thao T. Tran, Garden Grove, both of CA (US)

(73) Assignee: Allergan Sales, Inc., Irvine, CA (US)

( * ) Notice: Subject to any disclaimer, the term of this patent is extended or adjusted under 35 U.S.C. 154(b) by 0 days.

(21) Appl. No.: 09/262,623

(22) Filed: Mar. 4, 1999

(51) Int. Cl.[7] .............................. A61K 9/48; A61K 31/07; A61K 31/38

(52) U.S. Cl. ........................ 424/451; 424/452; 424/455; 514/432; 514/725

(58) Field of Search .................... 424/451, 452, 424/455; 514/432, 725

(56) References Cited

U.S. PATENT DOCUMENTS

| 4,612,194 | 9/1986 | Roshdy . |
|---|---|---|
| 5,656,289 | * 8/1997 | Cho et al. . |

FOREIGN PATENT DOCUMENTS

| 0 184 942 | 6/1986 | (EP) .............................. A61K/31/20 |
|---|---|---|
| 2960 | 11/1964 | (FR) . |

OTHER PUBLICATIONS

"Lipid–Based Vehicles for the Oral Delivery of Poorly Water Soluble Drugs" Humber Stone & Charman; Adv. Drug Delivery Reviews 25 (1997) 103–128.

Phyician's Desk reference Online, Vesanoid, revised Sep. 1998.*

* cited by examiner

*Primary Examiner*—Thurman K. Page
*Assistant Examiner*—Amy E Pulliam
(74) *Attorney, Agent, or Firm*—Walter A. Hackler

(57) ABSTRACT

A capsule system for oral delivery of an active agent having low aqueous solubility generally includes, in combination with the active agent, a vehicle for preventing initial active agent dissolution within the gastrointestinal tract and an emulsifier for promoting self-emulsification of the active agent and vehicle in the gastrointestinal tract. A capsule shell is provided for encapsulating the active agent, vehicle and emulsifier with the shell being formulated to open upon ingestion into the gastrointestinal tract and release the active agent and vehicle.

24 Claims, 1 Drawing Sheet

CAPSULE SYSTEM

The present invention generally relates to apparatus for encapsulating small doses of fluid contents and the contents themselves. More particularly, in a preferred embodiment, the present invention is directed to a gelatinous-like container system encompassing a single dose or charge of medication for oral administration.

A low aqueous solubility of a great number of medicaments is a source of inconvenience and further raises the overall cost of a course of treatment with any such low solubility medicament. Low aqueous solubility of a medicament often leads to low and unreliable systemic bioavailability.

Retinoids, that is, functional and structural derivatives of retinoic acid, have been successful in the treatment of acne, particularly nodular acne, psoriasis, disorders of Keratinion and oncology. However, the low aqueous solubility has limited the administration of the retinoids to their use in topical gels, creams, orals and the like.

A desired advantage of oral administration of retinoids is increased efficacy. Thus, in general, while the advantages of oral delivery or topical delivery of active agents are well known, oral administration of retinoids is made difficult by their low aqueous solubility, which results in decreased effectiveness in systemic drug delivery.

As set forth in an article by Humberstone and Charman, entitled, "Lipid-based Vehicles for the Oral Delivery of Poorly Water-Soluble Drugs", (Adv. Drug Del.Reviews 25, 1997, pp. 103–128), there are few commercial examples of lipid-based oral formulations, other than special cases, as for example, cyclosporin and the lipid-soluble vitamins. Reasons for the lack of commercial success include the complexity of the interfacial and physical chemistry. The article also reported that the results of different lipids and bioavailability are very drug specific. Accordingly, while the article appears to set forth general principles including emulsification techniques, there is, in fact, no general guidelines which can be relied on for developing an oral system for the delivery of a specific active agent, such as a retinoid, having low aqueous solubility.

In a preferred embodiment, the present invention is directed to a capsule system for the oral delivery of a retinoid having a low aqueous solubility and is more particularly directed to a capsule system for oral delivery of Tazarotene. The invention also includes a means for solubilizing retinoids and insuring effective systemic delivery of a retinoid drug.

In other words, the present invention provides a capsule system for active agents of low aqueous solubility in a form which is biologically available in a particularly advantageous way.

SUMMARY OF THE INVENTION

In a preferred embodiment, the present invention includes a capsule system for the oral delivery of an active agent having low aqueous solubility generally includes an active retinoid agent having low aqueous solubility and a vehicle for eliminating any need for initial active agent dissolution within the gastro-intestinal tract.

More particularly, the vehicle may comprise a liquid triglyceride which fully dissolves the active agent. In this manner, initial active agent dissolution within the gastro-intestinal tract is not necessary, because it is initially dissolved in the vehicle.

In addition, an emulsifier provides a means for promoting self-emulsification of the active agent and the vehicle in this gastro-intestinal tract. In the preferred embodiment, a capsuled shell provides a means for encapsulating the active agent vehicle means and emulsifier. The capsuled shell is formulated to open or dissolve upon ingestion into the gastro-intestinal tract and accordingly release the active agent and vehicle. At this point, the self-emulsification occurs thereby facilitating absorption through the gastro-intestinal wall thereby providing biological availability and systemic circulation of the active agent.

Preferably, the vehicle comprises a medium chain liquid triglyceride which, as hereinabove noted, initially, fully dissolves the active retinoid agent. More particularly, the vehicle may comprise a caprylic/capric triglyceride and the emulsifier may comprise co-emulsifiers, such as sorbitan monooleate and polysorbate 80. Other vehicles which may be suitable include: Ethyl oleate, Isopropyl myristate, Cetearyl octanoate, Corn oil, Cottonseed oil, Safflower oil, Olive oil, Peanut oil, Soybean oil and Sesame oil. Other emulsifiers which may be suitable include: Sorbitan monolaurate, Sorbitan monopalmitate, Sorbitan monostearate and Polysorbates 20, 40 or 60.

Importantly, the co-emulsifiers are selected to match a hydrophilic/lipophilic balance (HLB) of the caprylic/capric triglyceride. This is important in order to promote the optimal emulsification of the triglyceride into the aqueous gastro-intestinal fluids and accordingly the absorption of the agent for systemic circulation.

More specifically, as hereinabove noted, the active retinoid agent may be Tazarotene and the vehicle further comprises an antioxidant, such as, for example, butylated hydroxyanisole. Other antioxidants which may be suitable include: Butylated hydroxytoluene, Tocopherols (Vitamin E), Propyl gallate, and Ascorbyl palmitate. Other active retinoid agents include, for example, Vitamin A and its natural and synthetic derivatives.

A capsuled shell, as hereinabove noted, further includes an opaque colorant to prevent degradation of a retinoid, such as Tazarotene, from exposure of the capsule system to harmful wavelength of light.

Also a part of the invention is a method for enabling delivery of an active agent having low aqueous solubility. The method includes the steps of providing an active retinoid agent having low aqueous solubility with the active agent dissolved in a vehicle in order to eliminate any need for initial active agent dissolution in the gastro-intestinal tract.

The method further includes steps of incorporating an emulsifier to the vehicle in order to promote self-emulsification of the active agent and vehicle in the gastro-intestinal tract and the step of encapsulating the active agent, vehicle and emulsifier with a capsule shell formulated to open upon ingestion into the gastro-intestinal tract.

BRIEF DESCRIPTION OF THE DRAWING

The present invention may be more clearly understood with reference to the following detailed description in conjunction with the appended drawing, of which.

DETAILED DESCRIPTION

Figure 1:
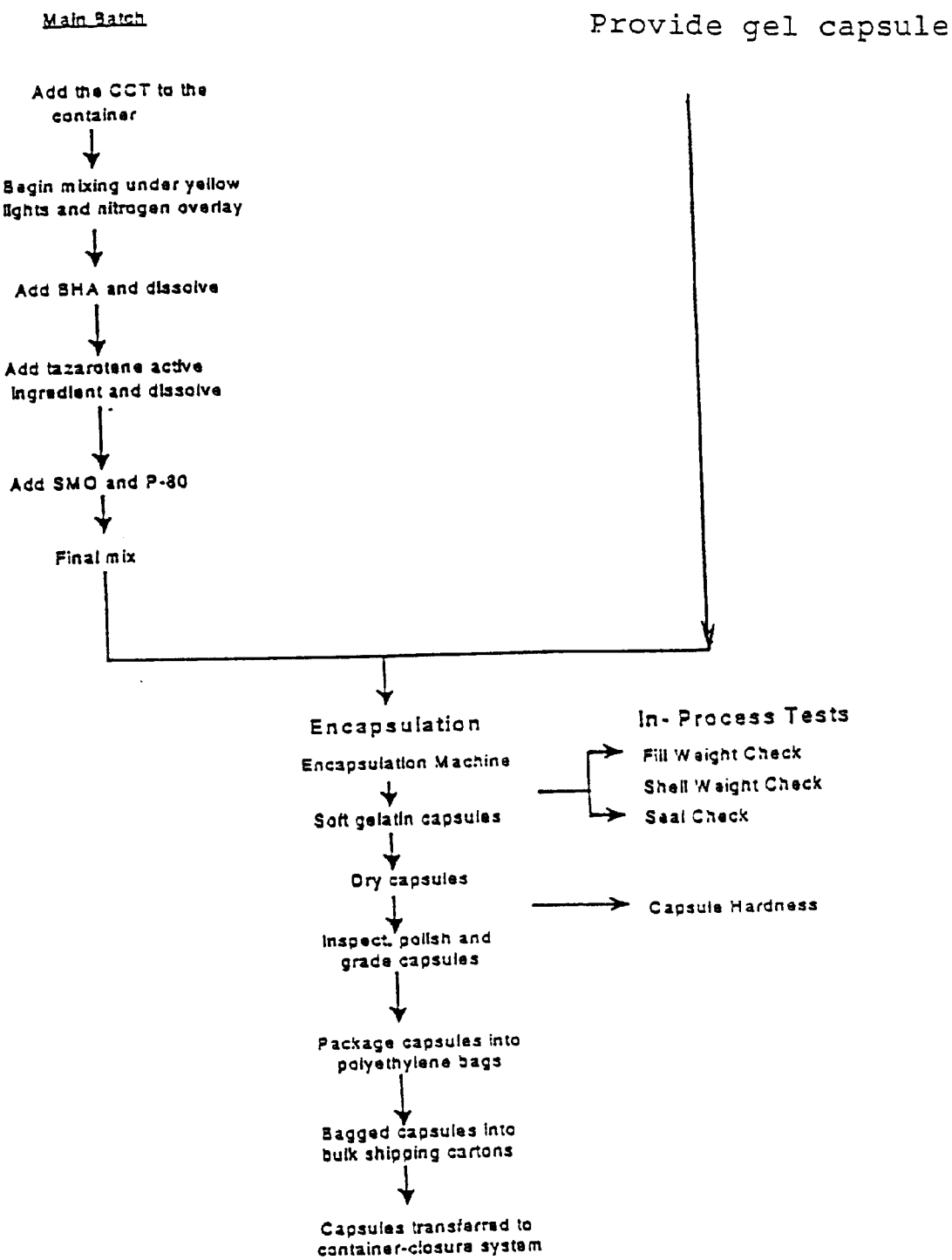
FIG. 1 is a manufacturing process flow chart for the capsule system in accordance with the present invention.

The invention is directed to capsule systems for the delivery of active agents, particularly retinoids. In a preferred example, it is known that the compound Tazarotene, known chemically as ethyl 6-[(4,4-dimethylthiochroman-6- yl)ethynyl]-nicotinate, having the molecular formula $C_{21}H_{21}NO_2S$, is active in the treatment of acne and psoriasis. Substantially increased activity of the active agent in this regard is expected if oral delivery can be effected. However, the solubility of Tazarotene in water is negligible.

The capsule of the present invention takes advantage of the tazarotene property of rapid systemic elimination (see $t_{1/2}$ in Table II), not exhibited by other currently available retinoids for acne and pssoriasis, such as isotretinoin, acitretin, and etretinate. The capsule of the present invention provides high and reliable oral absorption of tazarotene thus it produces effective therapeutic concentrations in man upon oral ingestion. The rapid system elimination is important for many patients, especially for women of child-bearing age. Upon cessation of oral tazarotene treatment, tazarotene is rapidly cleared from the body and poses little risks of teratogenic effects. The typical precautionary pregnancy wash-out periods for women of child-bearing age who just get off treatment of isotretinoin, acitretin, and etretinate are one month, three years, and for indefinite period of time, respectively.

In general, a capsule system in further accordance with the present invention includes a soft gelatin capsule containing an active retinoid having low aqueous solubility, such as Tazarotene, which is fully solubilized in a liquid triglyceride solution. The gelatin in accordance with the present invention may be derived from bovine sources which provides a capsule shell plasticized by, for example, glycerin.

Any suitable capsule shell formulation may be utilized which provides a means for not only encapsulating the retinoid active agent, but also for releasing same upon ingestion into a gastro-intestinal tract. It should also be appreciated that the system in accordance with the present invention may also contain conventional additional adjuvant substances which are conventionally used in the manufacture of drug capsules for providing consistency or facilitate the manufacture of the capsule. A lipophilic vehicle, such as a medium chain triglyceride, and more, specifically a caprylic/capric triglyceride is provided for active agent dissolution.

Importantly, the retinoid agent, Tazarotene, is fully dissolved in the vehicle in a conventional manner before incorporation into the capsule shell. The total dissolution of Tazarotene in the vehicle facilitates absorption from the gastro-intestinal tract by eliminating the need for drug dissolution prior to absorption. Utilizing caprylic/capric triglyceride has been found that up to about 34 mg of Tazarotene can be effectively solubilized in a capsule.

In other words, the Tazarotene is made particularly biologically available and can be absorbed by the body, although it is hard to dissolve in aqueous solutions, such as gastric juices.

Emulsifier means in accordance with the present invention is provided for promoting self-emulsion of the active agent and the vehicle in the gastro-intestinal tract. Preferably, emulsifier means includes a co-emulsifier system which matches the HLB requirements of the medium chain triglyceride, i.e., caprylic/capric triglyceride. This self-emulsion occurs in the gastro-intestinal tract following the gelatin shell opening.

More specifically, the co-emulsifier system includes sorbitan monooleate NF, and polysorbate 80 NF, which are commercially available.

Butylated hydroxyanisole NF (also commercially available), is added as an antioxidant to stabilize the Tazarotene. In addition, a colorant, such as, for example, titanium dioxide, is added to the shell formulation in order to provide protection of the Tazarotene from light which may otherwise cause degradation thereof. Otherwise, the shell may be conventionally formed of, for example, Gelatin and Glycerin.

The composition of two representative strengths of Tazarotene soft gelatin capsules is shown in Table 1.

A person skilled in the art would appreciate that the composition of the fill formulation shown in Table 1 may be altered somewhat to optimize the solubilization and/or emulsification of the drug. Additionally, the person of skill in the art would appreciate that the capsule systems and fill formulations disclosed herein would be suitable for retinoids other than Tazarotene.

TABLE 1

| Ingredient | Function | Concentration (mg/capsule) | |
| --- | --- | --- | --- |
| | | 0.7 mg Soft Gelatin Capsule (9096X) | 0.2 mg Soft Gelatin Capsule (9154X) |
| Fill Formulation: | | | |
| Tazarotene | Active | 0.70 | 0.20 |
| Burylated Hydroxyanisole NF | Anti-oxidant | 0.05 | 0.05 |
| Sorbitan Monooleate NF | Emulsifier | 5.0 | 5.0 |
| Polysorbate 80 NF | Co-emulifier | 0.25 | 0.25 |
| Medium-chain Triglycerides EP | Lipophilic vehicle | 94.0 | 94.5 |

Manufacturing Description with reference to FIG. 1.

The manufacture of the drug product involves three major manufacturing stages:

1. The manufacture of the triglyceride-based fill formulation.
2. Providing a gelatin capsule shell.
3. Soft gelatin encapsulation.

Details of each manufacturing stage is described in the following sections.

Manufacturing Directions
Manufacture of the Triglyceride-based Fill Formulation

1. Caprylic/capric triglyceride (CCT), which is a medium chain triglyceride, is weighed and added into a suitable mixing container.

2. Under yellow lights and a blanket of nitrogen, the following ingredients are added to the CCT while mixing, allowing each to fully dissolve before adding next:

Butylated Hydroxyanisole
Tazarotene (active pharmaceutical ingredient)

3. The following ingredients are then weighed and added sequentially.

Polysorbate 80 (P-80)
Sorbitan Monooleate (SMO)

4. The resulting bulk solution is mixed until homogeneous.

5. The batch is then encapsulated using the procedure described in Soft Gelatin Encapsulation.

Soft Gelatin Encapsulation

1. The encapsulation machine is of the rotary die type. It is fed by two receivers, one contains the molten gelatin mass used to form the shell, while the other contains the fill formulation.

2. The encapsulation machine provides a continuous form, fill, and seal operation.

a. The molten gelatin mass flows by gravity through heated tubes to two heated spreader boxes. The spreader boxes simultaneously cast the gelatin mass into two ribbons. These are lubricated with a blend of fractionated coconut oil/lecithin and delivered to the rotary dies.

b. The fill formulation flows by gravity into a hopper which serves as a reservoir to the input of the encapsulation pump. The fill formulation is delivered to the filling point by the positive displacement piston pump.

c. The two gelatin ribbons are fed in between the two rotating dies. The dies contain paired pockets which form the shape of the soft gelatin capsule and provide the sealing mechanism. At the precise moment that the two die pockets line up, the fill formulation is injected through an encapsulation wedge in between the gelatin ribbons. The seal forms as a result of the pressure between dies and heat applied by the encapsulation wedge to produce the soft gelatin capsule.

3. The capsules are then dried by a two phase process:

a. The capsules are moved to a rotary drier attached to the encapsulation machine. They are tumbled in a warm, low humidity, forced air environment for a predetermined length of time as specified in the batch records.

b. The second phase begins after discharge from the rotary drier the capsules are spread in a monolayer on shallow drying trays and low humidity air passed over them. Transfer of water to and from the shell occurs over several days until the water put into the gelatin during gelatin mass production has evaporated.

c. Capsule hardness determinations are performed to monitor the drying process. The capsules are monitored until the hardness is within the specified range. The capsules are then placed into deep holding trays.

4. Capsules are inspected and polished with V.M. & P. Naphtha to remove the lubricating film on the capsule surface, prior to grading and packaging.

Tazarotene soft gelatin capsules with the formulation set forth in Table 1 have currently been shown to be physically and chemically stable through twelve months of storage at 25° C. as well as six months storage at 40° C.

Table II, shows the plasma concentration of Tazarotene following dosing of the capsules set forth in Table I.

Although there has been hereinabove described a specific capsule system and method for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A capsule system for oral delivery of an active agent having low aqueous solubility, said capsule system comprising:

an active retinoid agent having low aqueous solubility consisting of Tazarotene;

vehicle means for initially dissolving the active agent;

emulsifier means for promoting self-emulsification of the active agent and vehicle means in the gastrointestinal tract; and capsule shell means for encapsulating the active agent, vehicle means, and emulsifier means as a non-emulsified, homogeneous mixture, said capsule shell means being formulated to open upon ingestion into said gastrointestinal tract and release the mixture, thus enabling self-emulsification of the vehicle means, with the active agent dissolved therein in the gastrointestinal tract.

2. The capsule system according to claim 1 wherein said vehicle means comprises a liquid medium chain triglyceride fully dissolving said active retinoid agent.

3. The capsule system according to claim 2 wherein said liquid medium chain triglyceride comprises caprylic/capric triglyceride.

4. The capsule system according to claim 2 wherein said vehicle means is selected from a group consisting of: Ethyl oleate, Isopropyl myristate, Cetearyl octanoate, Corn oil, Cottonseed oil, Safflower oil, Olive oil, Peanut oil, Soybean oil, and Sesame oil.

5. The capsule system according to claim 3 wherein said emulsifier means comprises coemulsifiers.

6. The capsule system according to claim 5 wherein said coemulsifiers comprise Sorbitan Monooleate and polysorbate 80.

TABLE II

Tazarotene Dosage Equivalents and Steady-State Pharmacokinetic Parameters of Tazarotenic Acid in Healthy Subjects

| Treatment | Dosage[1] (mg/kg/day) | Dosage[1] (mg/m²/day) | $C_{max}$ (ng/mL) | $t_{max}$ (hr) | $AUC_{0.24}$ (ng.hr/mL) | $t_{1/2}$[2] (hr) |
|---|---|---|---|---|---|---|
| 0.2 mg/day (with Ensure ®) | 0.003 | 0.12 | 5.24 ± 2.27 | 3.67 ± 1.51 | 30.6 ± 5.5 | NC[3] |
| 0.7 mg/day (with Ensure ®) | 0.010 | 0.40 | 19.9 ± 6.6 | 2.83 ± 0.98 | 101 ± 40 | 6.82 ± 1.66 |
| 0.7 mg/day (with water) | 0.010 | 0.40 | 18.9 ± 4.6 | 3.00 ± 1.55 | 94.1 ± 10.6 | 6.43 ± 1.67 |
| 1.4 mg/day (with Ensure ®) | 0.020 | 0.81 | 36.6 ± 8.5 | 1.83 ± 0.75 | 179 ± 39 | 9.41 ± 3.69 |
| 2.1 mg/day (with Ensure ®) | 0.030 | 1.21 | 44.3 ± 13.9 | 4.17 ± 2.04 | 219 ± 25 | 8.9 ± 1.7 |

Notes: Preliminary data following 5 days of once-daily dosing are presented
[1] = Assumes average subject weighs 70 kg and has surface area of 1.73 m²
[2] = Effective half-life; harmonic mean and pseudo-standard deviation reported.
[3] = Not calculable
Ensure ® is a liquid nutritional supplement that simulates food.

The results shown indicate effective levels of Tazarotene in plasma immediately following ingestion of the drug capsule system in accordance with the present invention when taken with and without a liquid nutritional supplement that simulates food. These plasma concentration levels may be sufficient to effect a treatment of acne in a patient.

7. The capsule system according to claim 5 wherein the coemulsifiers are selected from the group consisting of: Sorbitan monooleate, Sorbitan monolaurate, Sorbitan monopalmitate, Sorbitan monostearate, Polysorbate 20, Polysorbate 40, Polysorbate 60 and Polysorbate 80.

8. The capsule system according to claim 7 wherein said coemulsifiers are selected to match a hydrophilic/lipophilic balance of the caprylic/capric triglyceride.

9. The capsule system according to claim 1 further comprising an antioxidant present in said vehicle means.

10. The capsule system according to claim 9 wherein said capsule shell means further comprises an opaque colorant.

11. A capsule system for oral delivery of an active agent having low aqueous solubility, said capsule system comprising:
- an active retinoid agent having low aqueous solubility, the agent comprising Tazarotene present in an amount of up to about 34 mg/capsule;
- vehicle means for initially dissolving the active agent, said vehicle means comprising caprylic/capric triglyceride present in an amount of about 94% w/w;
- an antioxidant comprising butylated hydroxyanisole present in said vehicle means in the amount of about 0.05% w/w;
- emulsified means for promoting self-emulsification of the active agent and vehicle means in the gastrointestinal tract, said emulsifier means comprising, as coemulsifies, sorbitan monoleate present in an amount of about 5.0% w/w, and polysorbate 80 present in an amount of about 0.25% w/w; and
- capsule shell means for encapsulating the active agent, vehicle means, and emulsifier means, said capsule shell means being formulated to open upon ingestion into said gastrointestinal tract and release the active agent and vehicle means, said capsule shell means further comprising an opaque colorant.

12. A capsule system for oral delivery of an active agent having low aqueous solubility, said capsule system comprising:
- an active retinoid agent having low aqueous solubility consisting of Tazarotene;
- a liquid triglyceride fully dissolving said active agent;
- emulsifier means for promoting self-emulsification of the liquid triglyceride and dissolved active agent in a gastrointestinal tract; and
- capsule shell means for encapsulating the liquid triglyceride with dissolved active agent and emulsifier means as a non-emulsified, homogeneous mixture, said capsule shell means being formulated to open upon ingestion into said gastrointestinal tract and release the mixture, thus enabling self-emulsification of the liquid triglyceride and dissolved active agent in the gastrointestinal tract.

13. The capsule system according to claim 12 wherein said liquid triglyceride comprises caprylic/capric triglyceride.

14. The capsule system according to claim 13 wherein said emulsifier means comprises coemulsifiers.

15. The capsule system according to claim 14 wherein said coemulsifiers comprise Sorbitan Monooleate and polysorbate 80.

16. The capsule system according to claim 14 wherein said coemulsifiers are selected to match a hydrophilic/lipophilic balance of the caprylic/capric triglyceride.

17. The composition comprising the active agent liquid triglyceride and emulsifier means of claim 12.

18. The capsule system according to claim 13 further comprising an antioxidant present in said vehicle means.

19. The capsule system according to claim 18 wherein said capsule shell means further comprises an opaque colorant.

20. The capsule system according to claim 19 wherein the Tazarotene is present in the amount of between about 0.1 mg/capsule and about 34 mg/capsule, the antioxidant comprises butylated hydroxyanisole in the amount of about 0.05% w/w, the sorbitan monooleate is present in the amount of about 5.0% w/w capsule, the polysorbate 80 is present in the amount of about 0.25% w/w and the caprylic/capric triglyceride is present in the amount of about 94% w/w.

21. The composition comprising the Tazarotene, butylated hydroxyanisole, sorbitan monooleate, polysorbate 80 and caprylic/capric triglyceride of claim 20.

22. A method for enabling delivery of an active agent having low aqueous solubility, the method comprising the steps of:
- providing an active retinoid agent having low aqueous solubility consisting of Tazarotene;
- dissolving the active agent in a vehicle in order to eliminate initial active agent dissolution within a gastrointestinal tract;
- incorporating an emulsifier into the vehicle in order to promote subsequent self-emulsification of the active agent and vehicle in the gastrointestinal tract; and
- encapsulating the active agent, vehicle and emulsifier with a capsule shell formulated to open upon ingestion into said gastrointestinal tract.

23. The method according to claim 22 further comprising the step of incorporating an antioxidant into the vehicle.

24. The method according to claim 23 further comprising the step of incorporating an opaque colorant into the capsule shell.

* * * * *